(12) United States Patent
Nakahara et al.

(10) Patent No.: US 8,252,540 B2
(45) Date of Patent: Aug. 28, 2012

(54) DRUG DELIVERY SYSTEM TOWARD DEMYELINATING LESION AND BIOCHEMICAL MARKER OF DEMYELINATING LESION

(75) Inventors: Jin Nakahara, Tokyo (JP); Sadakazu Aiso, Tokyo (JP); Norihiro Suzuki, Tokyo (JP)

(73) Assignee: Keio University, Tokyo (JP)

( * ) Notice: Subject to any disclaimer, the term of this patent is extended or adjusted under 35 U.S.C. 154(b) by 165 days.

(21) Appl. No.: 12/671,856

(22) PCT Filed: Aug. 1, 2008

(86) PCT No.: PCT/JP2008/063838
§ 371 (c)(1),
(2), (4) Date: Apr. 16, 2010

(87) PCT Pub. No.: WO2009/020058
PCT Pub. Date: Feb. 12, 2009

(65) Prior Publication Data
US 2011/0250214 A1     Oct. 13, 2011

(30) Foreign Application Priority Data
Aug. 3, 2007 (JP) ................................. 2007-202776

(51) Int. Cl.
*G01N 33/53* (2006.01)

(52) U.S. Cl. ....................................................... 435/7.1

(58) Field of Classification Search .................. None
See application file for complete search history.

(56) References Cited

U.S. PATENT DOCUMENTS

| | | |
|---|---|---|
| 6,933,119 B2 | 8/2005 | Leppert et al. |
| 2003/0054397 A1 | 3/2003 | Leppert et al. |
| 2005/0089919 A1 | 4/2005 | Leppert et al. |
| 2005/0175998 A1 | 8/2005 | Nakahara et al. |
| 2006/0263783 A1 | 11/2006 | Podhajcer et al. |
| 2007/0178083 A1 | 8/2007 | Nakahara et al. |

FOREIGN PATENT DOCUMENTS

| | | |
|---|---|---|
| JP | 2003 504007 | 2/2003 |
| WO | 02 40996 | 5/2002 |
| WO | 03 011337 | 2/2003 |
| WO | 2005 007892 | 1/2005 |
| WO | WO 2008/085094 A1 | 7/2008 |

*Primary Examiner* — John Ulm
(74) *Attorney, Agent, or Firm* — Oblon, Spivak, McClelland, Maier & Neustadt, L.L.P.

(57) ABSTRACT

It is intended to provide a drug delivery system toward a demyelinating lesion. It is also intended to provide a biochemical marker of a demyelinating lesion. A delivery system for a prophylactic and/or therapeutic agent for a demyelinating disease characterized in that a substance capable of specifically recognizing Contactin is conjugated to an active ingredient of a prophylactic and/or therapeutic agent for a demyelinating disease is provided. Also provided is a method of evaluating and/or differentiating a demyelinating disease, including measuring the expression of Contactin in a body fluid.

6 Claims, 6 Drawing Sheets

DRUG DELIVERY SYSTEM TOWARD DEMYELINATING LESION AND BIOCHEMICAL MARKER OF DEMYELINATING LESION

CROSS REFERENCE TO RELATED APPLICATIONS

This application is a National Stage of PCT/JP08/063838 filed Aug. 1, 2008 and claims the benefit of JP 2007-202776 filed Aug. 3, 2007.

TECHNICAL FIELD

The present invention relates to a drug delivery system toward a demyelinating lesion and a biochemical marker of a demyelinating lesion. More specifically, the present invention relates to a technology directed to deliver a prophylactic or therapeutic agent for a demyelinating disease specifically to a demyelinating lesion and to biochemically evaluate and differentiate a demyelinating disease, using a molecule specifically expressed in a demyelinating lesion.

BACKGROUND ART

Multiple sclerosis (MS) is a demyelinating disease in the central nervous system, affecting an estimated 2.5 million people worldwide. In a typical example, demyelination occurs in a number of sites in the brain, the optic nerve, and the spinal cord in previously healthy adults in their 20 s and 30 s in the absence of particular induction, followed by development of various neurological symptoms corresponding to the foci (psychiatric disorders, palsy, visual loss, dizziness, and the like), which eventually disappear (remit) spontaneously. However, demyelination occurs again similarly (relapse) thereafter, by which patients suffer from neurological symptoms. The above-described course repeats itself many times, leaving sequelae over time, and patients become unable to walk on their own in many cases. Onset of MS itself is often unassociated with life prognoses; therefore, patients will suffer from numerous neurological sequelae for many years. Nowadays, a tendency of increase in the number of patients has been noted in Japan as well.

Causal treatment, or radical treatment, is most desired as a method of treating MS. It has been approximately 150 years since an overview of MS was proposed, during which techniques of molecular biology and the like have been developed and numerous genetic analyses have been performed. Yet, a cause of MS remains unknown and no radical treatment has been developed. A great number of pharmaceutical preparations have been developed with an aim of relapse prophylaxis and some of them have shown an effect of reducing a relapse rate to some extent; however, no treatment method to cure a disorder which has already manifested (for example, visual loss and palsy due to demyelination) has been developed yet. In view of the foregoing, development of remyelination therapy has come to be focused in Europe and the U.S., where a particularly large number of patients exist.

As noted above, MS is a disease which exhibits relapse (demyelination) and remission (spontaneous remyelination) and has such characteristics that remission becomes unable to be achieved over time and sequelae will remain (remyelination failure). Thus, it was speculated that oligodendrocytes, myelin sheath-forming cells, would disappear over time, and an attempt was made to develop neural stem cell transplant therapy for MS. On the other hand, it was reported in 1998 that a decrease in the number of oligodendrocytes was observed, while a large number of oligodendrocyte precursor cells (OPCs) remained in a demyelinating focus in MS (Non-Patent Document 1).

As of 1998, it had been elucidated that Fyn tyrosine kinase (Fyn)-mediated signal transduction was important for differentiation of OPCs (Non-Patent Document 2). It was also reported in 1999 that Fyn was essential for morphological differentiation of OPCs as well (Non-Patent Document 3). Furthermore, Nakahara et al. revealed that a γ chain of immunoglobulin Fc receptor (FcRγ) was expressed on OPCs (the expression disappeared upon completion of differentiation), and when the FcRγ on OPCs was indirectly cross-linked using IgG or the FcRγ itself was cross-linked in vitro, the expression of Fyn was increased and the strong phosphorylation of FcRγ-ITAM (Immunoreceptor Tyrosine-based Activation Motifs) by Fyn was induced, by which morphological and biochemical differentiation of OPCs was driven (Non-Patent Document 4 and Patent Document 1).

It has been pointed out that myelinolysis is involved in a number of neurological and mental diseases other than MS, such as senile dementia, Alzheimer's disease, spinal cord injury, and even diseases such as schizophrenia and manic-depressive illness; and therefore, remyelination therapy can potentially be established as a treatment method with a tremendous versatility, not only for MS.

Also, there has so far been no method to biochemically evaluate a demyelinated focus (i.e., a cluster of demyelinated nerve axons) in a living human, while indirect evaluation by MRI has been the only available option. Multiple sclerosis, which is a major demyelinating disease, is a characteristic disease exhibiting repetitive relapse and remission, and a type of disease called secondary-progressive multiple sclerosis is observed in patients with prolonged disease duration, in which clinical symptoms are slowly aggravated regardless of relapse. There are frequently cases in which it cannot necessarily be ascertained that neurological aggravation found upon consultation or self-reported aggravation in symptoms means relapse (MRI cannot necessarily visualize a relapsed lesion due to its detection limit). At present, whether or not treatment (mainly an intravenous infusion of steroid in Japan) should be given to a patient in whom aggravation as described above is suggested is up to each primary physician's discretion.

Non-Patent Document 1: Wolswijk G, J Neurosci 18:601-609, 1998
Non-Patent Document 2: Umemori H, et al. Nature 367:572-576, 1994
Non-Patent Document 3: Osterhout D J, et al., J Cell Biol 145:1209-1218, 1999
Non-Patent Document 4: Nakahara J, et al., Developmental Cell 4:841-852, 2003
Patent Document 1: International Publication WO03/011337 Pamphlet

DISCLOSURE OF THE INVENTION

Problems to be Solved by the Invention

An object of the present invention is to provide a drug delivery system toward a demyelinating lesion.

Further, an object of the present invention is to provide a biochemical marker of a demyelinating lesion.

Means for Solving the Problems

It is known that in the central nervous system (the brain, the spinal cord, and the optic nerve) and the peripheral nervous system, many of the nerve axons are wrapped in a myelin sheath, which is a lipid insulator, by which the conduction speed of electrical signal in the nerve axons is accelerated by 100-fold at maximum. In a demyelinating disease such as multiple sclerosis, the myelin sheath is broken down by a still-unidentified cause, which brings about blockade in the nerve conduction and damage to the nerve axons, resulting in a neurological disorder.

Various responses (inflammation, phagocytosis, cell proliferation, cell death, and the like) are observed around the demyelinated axons corresponding to a pathological condition, and control or activation of the above-described localized responses becomes crucial in treatment of a demyelinating disease. If such a drug delivery technique that causes neither an adverse reaction nor a side reaction in the normal brain and other organs except in demyelinating lesions is developed, it is considered that reduction in the dose of a therapeutic agent, suppression of adverse reactions and side reactions, and enhancement of an effect can be achieved.

A measure that can be contemplated to localize a certain therapeutic agent only in a demyelinating lesion is by identifying a molecule which is highly expressed only in the demyelinating lesion and delivering the therapeutic agent specifically to the lesion by using, as a carrier, a molecule capable of specifically conjugating to that molecule. Examples of the molecule which specifically conjugates to a certain molecule include a specific antibody against the molecule, the molecule itself (in the case of a molecule which exhibits homophilic conjugation), a receptor for the molecule, or an artificial compound having an affinity to the molecule.

The present inventors confirmed that Contactin molecules are highly expressed specifically in a human demyelinating lesion, and further confirmed that an anti-Contactin antibody accumulates in the human demyelinating lesion.

Further, in a clinical setting, the presence or absence of demyelination in the central nervous system is judged by an MRI examination, whereas that in the peripheral nervous system is judged by an electrophysiological examination. In the first place, graphic evaluation is only possible for severe demyelination in a tissue rich in myelin sheath (a white matter). However, graphic evaluation of demyelination is impossible in a tissue such as a gray matter where myelin sheaths play an important role regardless of their small amount and only little information is provided with regard to life and death of nerve axons in a demyelinating site (a possibility that nerve axons are damaged and necrotized at the same time with demyelination). Electrophysiological examination has such drawbacks that it lacks spatial quantitativity of demyelination, that the examination can be performed only for a nerve which is accessible from the body surface, and the like. In order to quantitatively or qualitatively evaluate the state of a demyelinating disease, or judge the presence or absence of a demyelinating lesion in a case in which demyelination cannot be confirmed on an image, or quantitatively analyze the increase or decrease of a demyelinating lesion in a clinical trial and the like, a molecule which is highly expressed specifically in nerve axons in a demyelinating lesion (if it is a molecule expressed in nerve axons, qualitative evaluation becomes possible because the molecule is not secreted by necrotized nerve axons) and which is secreted in a body fluid may be identified, and the concentration thereof in a body fluid measured to provide a simple as well as highly quantitative and qualitative method.

In clinical medicine, a technique of puncture in between the lumbar spines to collect a fluid in which the brain is immersed (cerebrospinal fluid) to examine the same is commonly and safely practiced. Thus, it is considered that if a protein which is specifically released into the cerebrospinal fluid from a demyelinating focus is discovered, evaluation of a demyelinating focus by the cerebrospinal fluid can be biochemically carried out.

The present inventors confirmed that Contactin molecules were highly expressed specifically in a demyelinating lesion and secreted in a body fluid, and its concentrations could be measured.

The present invention was completed based on the aforementioned findings.

A summary of the present invention is as follows;

(1) A delivery system for a prophylactic and/or therapeutic agent for a demyelinating disease, wherein a substance capable of specifically recognizing Contactin is conjugated to an active ingredient of a prophylactic and/or therapeutic agent for a demyelinating disease.

(2) The delivery system of (1), wherein the demyelinating disease is selected from the group consisting of congenital hypomyelinogenesis, a demyelinating disease in the central nervous system, a demyelinating disease in the peripheral nervous system, psychiatric disorder, post-radiation cephalopathy and post-chemotherapy cephalopathy.

(3) The delivery system of (1) or (2), wherein the substance capable of specifically recognizing Contactin is a specific antibody against Contactin.

(4) The delivery system of any one of (1) to (3), wherein the active ingredient of the prophylactic and/or therapeutic agent for a demyelinating disease is a substance capable of activating a γ chain of Fc receptors.

(5) The delivery system of (4), wherein the substance capable of activating a γ chain of Fc receptors is a ligand for a γ chain of Fc receptors, the ligand producing at least one effect selected from the following (A), (B) and (C):

(A) promoting the differentiation of oligodendroglial precursor cells;

(B) activating Fyn tyrosine kinase; and (C) promoting the expression of myelin basic protein.

(6) The delivery system of (5), wherein the ligand for FcRγ is a modified or unmodified anti-FcRγ antibody.

(7) A method of evaluating and/or differentiating a demyelinating disease, including measuring the expression of Contactin in a body fluid.

(8) The method of (7), wherein the demyelinating disease is selected from the group consisting of congenital hypomyelinogenesis, a demyelinating disease in the central nervous system, a demyelinating disease in the peripheral nervous system, psychiatric disorder, post-radiation cephalopathy and post-chemotherapy cephalopathy.

(9) The method of (7) or (8), wherein the body fluid is cerebrospinal fluid or blood.

(10) The method of any one of (7) to (9), wherein the expression of Contactin is measured at a protein level.

(11) The method of any one of (7) to (9), wherein the expression of Contactin is measured at an RNA level.

(12) A kit for evaluating and/or differentiating a demyelinating disease, containing a reagent capable of measuring the expression of Contactin in a body fluid.

(13) The kit of (12), wherein the demyelinating disease is selected from the group consisting of congenital hypomyelinogenesis, a demyelinating disease in the central nervous system, a demyelinating disease in the peripheral nervous system, psychiatric disorder, post-radiation cephalopathy and post-chemotherapy cephalopathy.

(14) The method of (12) or (13), wherein the body fluid is cerebrospinal fluid or blood.

(15) The kit of any one of (12) to (14), wherein the reagent is the following (i), (ii) or (iii):

(i) a specific antibody against Contactin;
(ii) a nucleic acid probe capable of specifically hybridizing with mRNA of Contactin; or
(iii) at least one pair of nucleic acid primers capable of specifically amplifying cDNA synthesized from mRNA of Contactin as a template.
(16) A pharmaceutical composition for preventing and/or treating a demyelinating disease, containing a substance capable of specifically recognizing Contactin conjugated to an active ingredient of a prophylactic and/or therapeutic agent for a demyelinating disease.
(17) A method of delivering an active ingredient of a prophylactic and/or therapeutic agent for a demyelinating disease to a demyelinating lesion, including administering to a subject an effective amount of the active ingredient of a prophylactic and/or therapeutic agent for a demyelinating disease, to which a substance capable of specifically recognizing Contactin is conjugated.
(18) A method of preventing and/or treating a demyelinating disease, including administering to a subject an effective amount of an active ingredient of a prophylactic and/or therapeutic agent for a demyelinating disease, to which a substance capable of specifically recognizing Contactin is conjugated.
(19) Use of an active ingredient of a prophylactic and/or therapeutic agent for a demyelinating disease as conjugated to a substance capable of specifically recognizing Contactin, for manufacture of pharmaceutical compositions for preventing and/or treating a demyelinating disease.

Advantages of the Invention

The present invention made it possible to deliver a prophylactic and/or therapeutic agent for a demyelinating disease specifically to a demyelinating lesion.

Also, the present invention made it possible to biochemically evaluate and differentiate a demyelinating disease.

The present specification encompasses the contents described in the specification and/or the drawings of Japanese Patent Application No. 2007-202776, based on which the present application claims priority.

BRIEF DESCRIPTION OF THE DRAWINGS

FIG. 3 is intended to detect the demyelinating lesion by luxol fast blue staining (sites decolorized into white: indicated by an arrow) and observe an accumulation of the anti-Contactin antibody in the demyelination lesion. As in FIGS. 1 and 2, it is understood that, in the brain of this patient, too, the anti-Contactin antibody accumulates in a demyelinating lesion which is generated by an ischemic cause. Demyelination caused by ischemic encephalopathy is a product of a non-specific reaction. Accordingly, it is suggested that a drug delivery targeting Contactin can be widely applied not only to multiple sclerosis but also to a general disease involving demyelination;

BEST MODE FOR CARRYING OUT THE INVENTION

Figure 1:
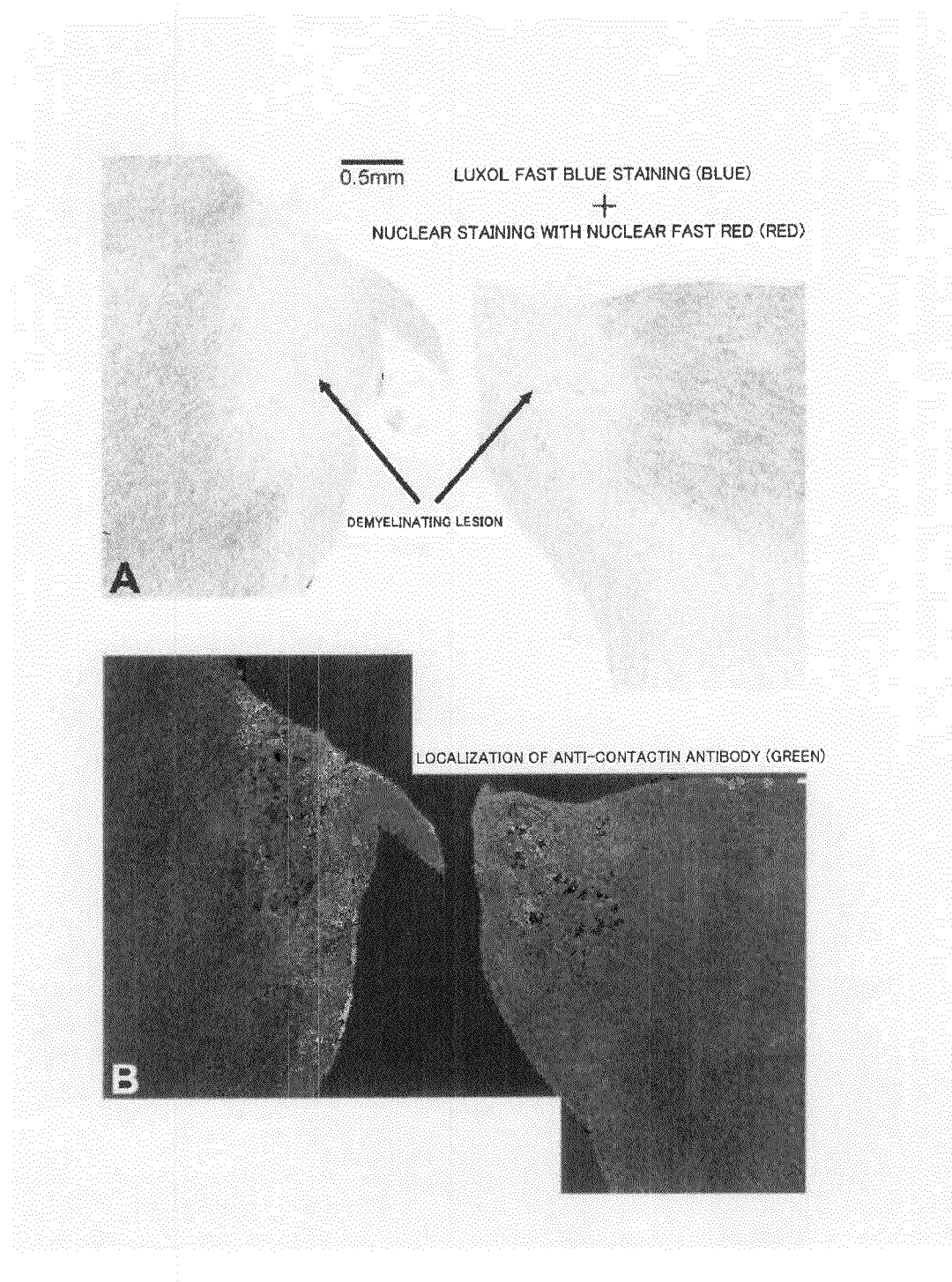
FIG. 1 shows a case of a brain of a patient with multiple sclerosis. Panel A detects demyelinating lesions (indicated by arrows), which are decolorized into white by luxol fast blue staining. Panel B shows a region adjacent to Panel A and was intended to observe if the anti-Contactin antibody would accumulate in a demyelinating lesion. As it is easily understood by comparing Panel B with Panel A, the anti-Contactin antibody is found to specifically accumulate in the demyelinating foci. A secondary antibody to which a fluorescent probe (FITC) has been added is used to confirm localization of the anti-Contactin antibody.

Embodiments of the present invention are described in detail hereinbelow.

The present invention provides a delivery system for a prophylactic and/or therapeutic agent for a demyelinating disease, characterized in that a substance capable of specifically recognizing Contactin is conjugated to an active ingredient of the prophylactic and/or therapeutic agent for a demyelinating disease.

The demyelinating disease can be exemplified by congenital hypomyelinogenesis (for example, adrenoleukodystrophy, metachromatic leukodystrophy, globoid cell leukodystrophy, Canavan's sclerosis, Pelizaeus-Merzbacher disease, Alexander's disease, and cerebral palsy), a demyelinating disease in the central nervous system (for example, multiple sclerosis (including neuromyelitis optica and concentric sclerosis), acute disseminated encephalomyelitis, inflammatory diffuse sclerosis, subacute sclerosing panencephalitis, progressive multifocal leukoencephalopathy, cerebral hypoxia, central pontine myelinolysis, vitamin B12 deficiency, Binswanger's disease, cerebral infarction, spinal cord infarction, demyelinating lesion accompanying to changes associated with aging, and spinal cord injury), a demyelinating disease in the peripheral nervous system (for example, Guillain-Barre syndrome, Fisher syndrome, chronic inflammatory demyelinating polyradiculoneuropathy, and neuropathy accompanying demyelination), a psychiatric disorder (for example, Alzheimer's disease, schizophrenia, manic-depressive illness, and age-related dementia), post-radiation leukoencephalopathy, post-chemotherapy leukoencephalopathy, and the like; however, the demyelinating disease is not limited to these examples.

Contactin is a cell adhesion molecule belonging to immunoglobulin superfamily (Ig-CAM) consisting of six Ig domains and four FNIII domains (amino acid sequence (NCBI accession number: AAH36569), mRNA/cDNA sequence (NCBI accession number: BC036569), and genetic information (NCBI gene ID: 1272) etc). Regarding functions of Contactin, for example, Contactin has been reported to regulate growth and branching of neurites by coupling with other Ig-CAMs, cell adhesion molecules, and the like, and to contribute to constituting nodes of Ranvier by coupling with other cell adhesion molecules, channels, and the like in a myelinated nerve (Falk J, et al. Bio Cell 94:327-334, 2002).

A substance capable of specifically recognizing Contactin can be exemplified by a specific antibody against Contactin, Contactin itself, a receptor for Contactin, an artificial compound having an affinity to Contactin, and the like; however, the substance is not limited to these examples.

The specific antibody against Contactin can be either a polyclonal antibody or a monoclonal antibody, for example, a goat polyclonal anti-Contactin antibody (a product of Santa Cruz Biotechnology, Inc.), a goat polyclonal anti-Contactin antibody (a product of R&D systems, Inc.), a mouse monoclonal anti-Contactin antibody (a product of R&D systems, Inc.), a mouse monoclonal anti-Contactin antibody (a product of Becton, Dickinson and Company), a mouse monoclonal anti-Contactin antibody (a product of UC Davis/NINDS/NIMH NeuroMab Facility), and a rabbit polyclonal anti-Contactin antibody (a product of Chemicon International, Inc.) can be obtained and used in the present invention. Also, those prepared by ordinary methods can be used.

As Contactin, recombinant human Contactin (a product of R&D systems, Inc.) and the like are available and can be used in the present invention. Also, those prepared as recombinant proteins or synthesized peptides by ordinary methods based on the published amino acid sequence (NCBI accession number: AAH36569), mRNA/cDNA sequence (NCBI accession number: BC036569), genetic information (NCBI gene ID: 1272), and the like can be used.

As the receptor for Contactin, Neurofascin-155, Caspr/Paranodin, Nr-CAM, Neurofascin-186, Tenascin family (including Tenascin-R), Phosphacan, a Na channel, RPTPb (Falk J, et al. Bio Cell 94:327-334, 2002), Notch (Hu Q D et al. Cell 115:163-175, 2003), and the like are known, and can be used in the present invention.

The artificial compound having affinity to Contactin can be exemplified by a recombinant protein in which only a part of amino acids obtainable by a Contactin gene is expressed or modified, a recombinant protein in which only a part of amino acids obtainable by a gene of the group containing receptors for Contactin as listed above and the like is expressed or modified, a synthesized peptide which is presumed to have a conjugating property based on the amino acid sequence and three-dimensional structure of Contactin, and the like.

The active ingredient of a prophylactic and/or therapeutic agent for a demyelinating disease includes a substance capable of activating the γ chain of Fc receptors. Such a substance is considered to initiate myelin formation by giving an OPC an FcRγ signal (refer to International Publication WO03/011337). However, because FcRγ is expressed in the immune cells as well, the concern of adverse reactions is raised in association with practical application of a medicine which induces remyelination via stimulation of FcRγ. Accordingly, it is considered necessary to construct a system by which the pharmaceutical agent is selectively delivered only to a demyelinating lesion in order to alleviate adverse reactions. In light of the above, application of the drug delivery system of the present invention enables specific delivery of the pharmaceutical agent to the demyelinating lesion, by which alleviation of adverse reactions is anticipated, and further, reduction in the dose of a medicine necessary to exert a clinical effect can be anticipated. The substance capable of activating a γ chain of Fc receptors is a ligand for a γ chain of Fc receptors, and preferably the ligand produces at least one effect selected from the following (A), (B) and (C):
(A) promoting the differentiation of oligodendroglial precursor cells;
(B) activating Fyn tyrosine kinase; and
(C) promoting the expression of myelin basic protein.

Alternatively, the substance can be one which does not necessarily have any of the effects of (A) to (C) as long as it is a substance which promotes myelin formation by specifically conjugating to FcRγ. A ligand for the γ chain of Fc receptors can be exemplified by an anti-γ chain of Fc receptors antibody (hereinafter described as "anti-FcRγ antibody"), a modified form thereof, and the like. The anti-FcRγ antibody includes a polyclonal antibody and a monoclonal antibody.

Commercial products such as a rabbit polyclonal anti-FcRγ antibody (a product of Upstate Biotechnology, Inc.) and those prepared by ordinary methods can be used as the anti-FcRγ antibody.

For example, to prepare a polyclonal antibody, an animal can be immunized by inoculation with an immunizing antigen, FcRγ. Then, an anti-FcRγ antibody-containing substance can be collected from the immunized animal, followed by separation and purification of the antibody. Alternatively, a partial peptide of FcRγ can be used. Further, immunization can be carried out using an artificial peptide which is synthesized based on a prediction drawn from a base sequence of FcRγ (GenBank M33195 (in the case of a human)). In that case, if a short peptide (generally having 6 to 18 amino acid residues) is used as an immunogen, it can be prepared as a complex with a carrier protein such as Keyhole limpet haemocyanin. Normally, in the case of administration of a protein, 50 to 100 μg are used for immunization.

To prepare a monoclonal antibody, an individual having a high antibody titer is selected from among the aforementioned immunized animals and a spleen or a lymph node is collected three to five days after a final immunization. Then, an antibody-producing cell contained therein is fused with a myeloma cell, after which a hybridoma stably producing an antibody of high titer is selected. The hybridoma can be intraperitoneally proliferated in an animal and a monoclonal antibody can be purified from the ascites, or a monoclonal antibody can be purified from a serum of the animal and the like. Alternatively, a hybridoma can be cultured in a medium and allowed to produce a monoclonal antibody, after which the monoclonal antibody can be purified from a culture supernatant and the like. A method for producing a monoclonal antibody is described in P. N. Nelson et al., J. Clin. Pathol.: Mol. Pathol. 53, 111-117 (2000), which is incorporated in the present specification as a reference.

A method for preparing FcRγ as an immunogen is described in a paper by Takai et al. (T. Takai, M. Li, D. Sylvestre, R. Clynes, J. V. Ravetch, Cell 76, 519 (1994)) or in the literature cited in the paper, all of which are incorporated in the present specification as references. In the case of a human, a synthesized peptide is readily produced based on a publicly available sequence of human FcRγ (GenBank M33195 (in the case of a human)).

When immunizing an animal, FcRγ as an immunogen is administered singly or with a carrier or a diluent to an animal (for example, a mammal) in a site where an antibody can be produced upon administration. As to administration, administration by subcutaneous injection is preferable. At administration, a complete Freund's adjuvant or an incomplete Freund's adjuvant can be administered in order to enhance the antibody productivity. Normally, administration can be conducted once a week, and once or twice a week in the case of a monoclonal antibody, and three or four times a week in the case of a polyclonal antibody.

Animals to be immunized include, for example, monkey, rabbit, dog, guinea pig, mouse, rat, sheep, goat, chicken and the like.

The antibody is collected from the blood, the ascites, and the like of the animals immunized as described above. A method most frequently used for measuring an antibody titer is ELISA (Enzyme Linked Immunosorbent Assay). In order to further study in detail, immunocytochemistry and Western blot can be conducted. For detail, a paper by Nelson et al. (P. N. Nelson et al., J. Clin. Pathol.: Mol. Pathol. 53, 111-117 (2000)) can be referred to.

Separation and purification of the antibody can be carried out according to methods for separating and purifying an immunoglobulin (for example, a salting-out method, an alcohol precipitation method, an isoelectric point precipitation method, an electrophoresis method, an adsorption-desorption method using an ion-exchanger (for example, DEAE), a ultracentrifugation method, a gel filtration method, and a specific purification method in which only a specific antibody is collected by an antigen-binding substance or an activated adsorption agent such as protein A, followed by dissociation of the conjugation to obtain the antibody).

The antibody thus prepared contains IgG as a main component, while including other immunoglobulins such as IgM and IgA. The antibody thus prepared specifically conjugates to FcRγ.

A hybridoma producing an anti-FcRγ antibody can be prepared by selecting an individual which is confirmed to have an antibody titer from among animals such as a mouse immunized as in the above described method for preparing a polyclonal antibody and collecting a spleen or a lymph node within one week of final immunization, and then fusing an antibody-producing cell contained therein with a myeloma cell. The operation of fusion can be conducted according to known methods such as the method of Kohler and Milstein (Nature, 256, 495 (1975)). Polyethylene glycol (PEG) and a Sendai virus can be used as a fusion—accelerating agent, among which PEG is preferably used. As a myeloma cell, Sp2/0, NS1, NSO, X63Ag8 and the like may be mentioned, among which Sp2 and the like are particularly preferably used. A preferable ratio between the number of antibody-producing cells (spleen cells) to the number of myeloma cells used is approximately 1:1 to 1:2, and cell fusion is efficiently conducted by adding PEG (preferably PEG1000 to PEG6000) approximately at a concentration of 50% and incubating the cells at 37° C. for 20 to 30 minutes.

Separation and purification of the monoclonal anti-FcRγ antibody is carried out according to a separation and purification method of an immunoglobulin as in the separation and purification of the polyclonal antibody described above.

The anti-FcRγ antibody can be one that belongs to any of the classes of IgG, IgA, and IgM as long as it specifically conjugates to FcRγ and displays a desired effect. Also, the anti-FcRγ antibody can be Fab' or a Fab fraction which is obtainable by removing Fc or an Fc region from the aforementioned immunoglobulins, or a polymer thereof. Further, a chimeric antibody which is expressed as a recombinant obtained by fusing a variable gene segment of the anti-FcRγ antibody and a constant gene of a human immunoglobulin can be used.

Furthermore, the anti-FcRγ antibody can be modified with such a sugar chain that is degradable by an enzyme present in the brain.

Other than the anti-FcRγ antibody, a substance capable of activating FcRγ can be exemplified by the following.
1) An anti-FcγRI antibody
2) An anti-FcγRIII antibody
3) An antagonist of FcγRII
4) An artificial compound which is anticipated to have a conjugating ability with FcRγ based on the structure of FcRγ
5) A subclass of IgG which has a high conjugating property to FcγRI among IgGs
6) An anti-FcεRI antibody.

The anti-FcγRI antibody of 1) and the anti-FcγRIII antibody of 2) can be prepared in accordance with the above described method for preparing the anti-FcRγ antibody, using FcγRI and FcγRIII as an immunogen, respectively.

The antagonist of FcγRII of 3) may be one having an effect of inhibiting a function that acts suppressively (negatively) against FcRγ.

As FcγRII (Fc receptor II) acts suppressively against an FcRγ activity, it is considered that an enhanced effect can be obtained if FcγRII is blocked by an antagonist prior to stimulation of FcRγ.

The artificial compound which is anticipated to have a conjugating ability with FcRγ based on the structure of FcRγ of 4) can be one which is capable of activating FcRγ, and the conjugating ability with FcRγ can be anticipated by IP-Western and the like. For example, the compound is reacted with an oligodendroglia and then IP (immunoprecipitation) is carried out using an FcRγ antibody, and subsequently if a substance thus obtained is found to be the artificial compound, the compound is presumed to have the conjugating ability. The artificial compound which is anticipated to have a conjugating ability with FcRγ as described above can be either purchased from the market or chemically synthesized.

The subclass of IgG which has a high conjugating property to FcγRI among IgG of 5) can be exemplified by IgG3, IgG1, IgG4, IgG2 and the like in the case of a human. In the case of a mouse, it can be exemplified by IgG2a, IgG1, IgG2b, IgG3, and the like. FcγRI is a high-affinity IgG receptor, whereas FcγRIII is a low-affinity IgG receptor. In view of the above, in order to activate FcγRI, a subclass of IgG which has a high conjugating ability with FcγRI can be selectively administered, which is typically IgG3 in the case of a human. J. E. Gessner et al., Ann. Hematol. 76, 231-248 (1998) can be referred to as a relevant review. The subclasses of IgG as described above can be prepared by mixing an IgG obtained from a monoclonal hybridoma whose subclass has been specified so as to make a mixture of polyclonal antibodies, or by obtaining an antibody from a nonreactive hybridoma.

The anti-FcεRI antibody of 6) can be prepared in accordance with the method for preparing the anti-FcRγ antibody as described above, using FcεRI as an immunogen.

An active ingredient of a prophylactic and/or therapeutic agent for a demyelinating disease can be used singly or several kinds thereof can be used in combination.

Furthermore, if the demyelinating disease is a viral demyelinating disease (such as progressive multifocal leukoencephalopathy (lethal) caused by a JC virus), the drug delivery system of the present invention is considered applicable in selective delivery of an anti-virus drug to a demyelinating region, and the like. Thus, it is considered that the drug delivery system of the present invention can potentially be developed as a general drug delivery system, in addition to the drug delivery system exemplified above. In that case, an active ingredient of a prophylactic and/or therapeutic agent for a demyelinating disease includes active ingredients of anti-viral drugs (for example, HARRT, azidothymidine, interferon α, interferon β, ribavirin, an anti-virus antibody, and the like).

In the drug delivery system of the present invention, a substance capable of specifically recognizing Contactin is conjugated to an active ingredient of a prophylactic and/or therapeutic agent for a demyelinating disease. Conjugation of a substance capable of specifically recognizing Contactin to an active ingredient of a prophylactic and/or therapeutic agent for a demyelinating disease can be achieved as follows. For example, conjugation of an anti-Contactin antibody to an anti-FcRγ antibody which promotes remyelination can be conducted by preparing both antibodies or F(ab) fragments of both antibodies and chemically cross-linking them by N-succinimidyl-3-(2-pyridyldithiol)-propionate (SPDP) and succinimidyl-4-(p-maleimidophenyl)-butyrate (SMPB), or by fusing hybridomas which serve as original sources of both antibodies to produce a fusion antibody by genetic recombination, and the like (Segal D M et al., Curr Prot Immunol 2.13.1-2.13.16, 1995). Similarly, in the case of a substance other than an anti-Contactin antibody that is capable of specifically recognizing Contactin and in the case of an active ingredient other than an anti-FcRγ antibody in a prophylactic and/or therapeutic agent for a demyelinating disease, the substance capable of specifically recognizing Contactin can be conjugated to the active ingredient of a prophylactic and/or therapeutic agent for a demyelinating disease using chemical cross-linking or genetic engineering techniques.

When a prophylactic and/or therapeutic agent for a demyelinating disease is administered orally or parenterally to a subject such as a mammal (for example, human, rabbit, dog, cat, rat, or mouse) using the drug delivery system of the present invention, a substance capable of specifically recognizing Contactin conjugated to an active ingredient of a prophylactic and/or therapeutic agent for a demyelinating disease can be administered singly or by formulating it into a pharmaceutical composition of an appropriate dosage form together with a pharmacologically acceptable carrier, a diluent, or an excipient. The dose varies depending on the subject or recipient, the disease to be treated, the symptom, the administration route, and the like, for example, in the case of using the prophylactic and/or therapeutic agent for prophylaxis or treatment of an adult demyelinating disease (for example, multiple sclerosis), an anti-FcRγ antibody or a modified form thereof (to which a substance capable of specifically recognizing Contactin is conjugated) can be administered normally at approximately 150 to 500 mg/kg body weight, preferably at approximately 400 to 500 mg/kg body weight per dose approximately once or twice per month, preferably consecutively for two to three days at the same dose at the initiation of treatment, by intravenous injection. Also, in other cases of parenteral administration and oral administration, a dose according to the above can be administered. In the case when the symptom is particularly severe, the dose can be increased accordingly.

Compositions for oral administration include solid or liquid dosage forms, which specifically include a tablet (including a sugar-coated tablet and a film-coated tablet), a pill, a granule, a powder, a capsule (including a soft capsule), a syrup, an emulsion, a suspension, and the like. Such compositions can be produced by an ordinary method and can contain a carrier, a diluent, or an excipient which is normally employed in the field of drug formulation. For example, carriers or excipients for tablets include lactose, starch, sucrose, and magnesium stearate.

Compositions for parenteral administration include, for example, an injection and a suppository, and an injection can be formulated as an intravenous injection, a subcutaneous injection, an intradermal injection, an intramuscular injection, an infusion injection, and the like. Such injections are prepared by an ordinary method, namely, by dissolving, suspending, or emulsifying an active ingredient of a prophylactic and/or therapeutic agent for a demyelinating disease in a sterile aqueous or oily solution which is normally used for injections. Aqueous solutions for injection include physiological saline, an isotonic solution containing glucose and other adjunctive medicines, and the like, and these can be used in combination with an appropriate solubilizing agent, such as alcohol (for example, ethanol), polyalcohol (for example, propylene glycol and polyethylene glycol), and a nonionic surfactant (for example, polysorbate 80, HCO-50 (polyoxyethylene (50 mol) adduct of hydrogenated castor oil). Oily solutions include sesame oil and soybean oil, and it can be used in combination with benzyl benzoate, benzyl alcohol, and the like as a solubilizing agent. The prepared injection liquid is normally filled in an appropriate ampoule. A suppository for rectal administration can be prepared by mixing an active ingredient of a prophylactic and/or therapeutic agent for a demyelinating disease with a base normally used in suppositories. As to parenteral administration of a prophylactic and/or therapeutic agent for a demyelinating disease, a case in practice is such that the pharmaceutical agent is directly infused into the spinal fluid (Science. 1981 Nov. 27; 214 (4524): 1026-8), and the prophylactic and/or therapeutic agent of the present invention can also be delivered to a demyelinated site by such a method.

The oral or parenteral pharmaceutical composition as described above can be prepared into a dosage form of such a dosage unit that conforms to the dose of an active ingredient. Dosage forms of such a dosage unit include a tablet, a pill, a capsule, an injection (an ampoule), and a suppository. While the amount of an active ingredient incorporated varies with the kind of formulation, it is normally 1 to 100% by weight, and preferably 50 to 100% by weight.

Furthermore, the present invention provides a method of evaluating and/or differentiating a demyelinating disease, including measuring the expression of Contactin in a body fluid.

The demyelinating disease is as described above.

The body fluid can be exemplified by the cerebrospinal fluid, the blood, and the like.

Evaluation of a demyelinating disease refers to a concept encompassing a quantitative or qualitative evaluation of the state of a demyelinating disease, judgment of the presence or absence of a demyelinating lesion, and quantitatively analyzing the increase and decrease of a demyelinating lesion in a clinical trial and the like.

Differentiation of a demyelinating disease refers to a concept encompassing differentiation of relapse, remission, and secondary-progressive type of multiple sclerosis.

Further, the method of the present invention can potentially be used for evaluation and differentiation of a cerebral ischemic lesion (including cerebral infarction and ischemic leukoaraiosis developed in connection with aging, which can be a cause of dementia).

In the method of the present invention, either the expression of Contactin in a body fluid sample or the gene expression thereof can be measured. For example, it can be measured by Northern blotting, RT-PCR, Western blotting, immunohistochemical analysis, and the like. Alternatively, it can be measured using cDNA microarray, ELISA, and the like.

In order to measure the expression of Contactin at a protein level, a specific antibody against Contactin may be used. The antibody can be either a monoclonal antibody or a polyclonal antibody, both of which can be prepared by a publicly known method. When measurement is conducted by Western blotting, the antibody is secondarily detected using I-labeled protein A, peroxidase-conjugated IgG, and the like. When measurement is conducted by an immunohistochemical analysis, the antibody can be labeled with a fluorescent dye, ferritin, an enzyme, and the like.

In order to measure the gene expression of Contactin at an RNA level, a nucleic acid probe capable of specifically hybridizing with mRNA of Contactin can be used (in a case when measurement is conducted by Northern blotting). Alternatively, at least one pair of nucleic acid primers capable of specifically amplifying cDNA synthesized from mRNA of Contactin as a template can be used (in a case when measurement is conducted by RT-PCR). The nucleic acid probe and the nucleic acid primer can be designed based on genetic information of Contactin (an mRNA/cDNA sequence (NCBI accession number: BC036569), genetic information (NCBI gene ID: 1272), and the like). Normally, the nucleic acid probe is appropriately about 15 to 1500-base-long. The nucleic acid probe can be labeled with a radioactive element, a fluorescent dye, an enzyme, and the like. Normally, the nucleic acid primer is appropriately about 15 to 30-base-long.

When using ELISA, the following example may be mentioned, a body fluid sample (for example, cerebrospinal fluid) of a subject is dropped onto a solid phase (for example, a substrate such as a microtiter plate) to which a polyclonal anti-Contactin antibody (a capture antibody) is adsorbed, and Contactin conjugated with the capture antibody is then reacted with a monoclonal anti-Contactin antibody (a detector antibody), followed by a reaction with an enzyme-labeled anti-IgG antibody (a secondary antibody), and subsequently, a substrate of the enzyme (normally, a coloring or luminescent reagent) is added to detect a product of an enzyme reaction.

When using cDNA microarray, the following example may be mentioned, mRNA extracted from a body fluid sample (for example, cerebrospinal fluid) of a subject is converted to cDNA by reverse transcriptase and labeled with a biotin and the like, and subsequently, it is hybridized with a nucleic acid probe immobilized on a substrate (for example, a glass substrate), and fluorescent intensity is measured.

In the present invention, either the presence or absence of the expression of Contactin in a cerebrospinal fluid sample of a subject and/or the gene expression thereof may be detected, or, the expression level thereof may be measured. The presence or absence of the expression of Contactin and/or mRNA thereof is confirmed by the appearance or non appearance of a spot or band in predetermined positions. The expression level of Contactin and/or mRNA thereof can be measured in terms of the staining intensity of the spot or band. Alternatively, Contactin and/or mRNA thereof can be quantitated.

While the subject is a patient suspected of suffering from a demyelinating disease, all humans who are considered to be at the risk of developing the disease can be targeted.

The cerebrospinal fluid is a fluid in which the brain is immersed, which can be collected by puncture in between the lumbar spines. This method is commonly and safely practiced.

Blood can be collected by puncture in the vein or the artery and this commonly and safely practiced.

As an example of the present invention, evaluation and/or differentiation of a demyelinating disease can be conducted according to the standard described below. When the concentration of Contactin in the cerebrospinal fluid is quantitatively evaluated in a patient who is suspected of having an unidentified brain disease and whose symptoms are stable, the patient is judged to have a disease not involving demyelination or to be normal in a case when the concentration is a negative value not more than the detection limit (less than 0.1 ng/ml). If the concentration is 0.1 ng/ml or above, the patient is judged to have a demyelinating disease. The higher the above value is, the area of demyelination is judged to be the wider (severer). Alternatively, in the case of a patient who has been judged to have a demyelinating disease (for example, relapsing-remitting multiple sclerosis), if a change in the disease condition cannot be detected by various examinations including imaging although aggravation in the symptoms is subjectively and objectively suspected, the disease condition is judged to have changed if the concentration of Contactin in cerebrospinal fluid is significantly fluctuated compared to a previous value. Alternatively, in the case of a patient suffering from a disease such as cerebral infarction, if the concentration of Contactin in cerebrospinal fluid is significantly high in the patient, it is indicated that demyelinated axons remain in the brain of the patient, allowing for a judgment that long-term recovery can be expected.

The present invention also provides a kit for evaluating and/or differentiating a demyelinating disease, containing a reagent capable of measuring the expression of Contactin in a body fluid.

The demyelinating disease and the body fluid are as described above.

As an example, the kit of the present invention contains a specific antibody against Contactin as a reagent. The antibody may be immobilized on a substrate. The kit may further contain a device to collect a body fluid, a set of reagents and assay devices for immunochemically detecting Contactin, an instruction manual, and the like. In additions to the directions for use of the kit, a standard for evaluation and differentiation of a demyelinating disease and the like are preferably described in the instruction manual.

As another example, the kit of the present invention contains a nucleic acid probe capable of specifically hybridizing with mRNA of Contactin as a reagent. The nucleic acid probe may be immobilized on a substrate. The kit may further contain a device to collect a body fluid, reagents to extract RNA from a body fluid sample, reagents and assay devices for analyzing RNA by Northern blotting, an instruction manual, and the like. In additions to the directions for use of the kit, a standard for evaluation and differentiation of a demyelinating disease and the like can be described in the instruction manual.

Further, as another example, the kit of the present invention contains, as a reagent, at least one pair of nucleic acid primers capable of specifically amplifying cDNA synthesized from mRNA of Contactin as a template. The kit may further contain a device to collect a body fluid, reagents to extract RNA from a cerebrospinal fluid sample, reagents and assay device for analyzing RNA by RT-PCR, an instruction manual, and the like. In addition to the directions for use of the kit, a standard for evaluation and differentiation of a demyelinating disease and the like can be described in the instruction manual.

EXAMPLES

The present invention is described in detain hereinbelow based on Examples; however, the present invention is not limited to these Examples.

Example 1

Drug Delivery System Toward Demyelinating Lesion

Method

Four cases of postmortem brains of patients with no encephalopathy, 10 cases of postmortem brains of patients with demyelinating lesions due to multiple sclerosis, and one case of postmortem brain of a patient with a demyelinating lesion associated with an ischemic change (all specimens were fresh, unfixed frozen white matters that had passed nine to 58 hours since death) were provided by the Human Brain and Spinal Fluid Resource Center in Los Angeles, Calif., U.S.A. The brain specimens were transported from the Center by air while kept frozen on dry ice, and preserved in a freezer at −80° C. immediately upon arrival at a laboratory in Department of Anatomy, School of Medicine, Keio University. Sampling sites of each brain specimen were cut while being frozen, and small specimens thus obtained were fixed by immersing in 4% paraformaldehyde phosphate-buffer solution (a product of Wako Pure Chemical Industries, Ltd.) for 20 hours while being refrigerated. Upon completion of fixation, the fixation liquid was removed by immersing the specimens in phosphate-buffer saline of pH 7.4 (PBS: a product of Ambion, Inc.) for a total of three times, each continuing for three minutes, at room temperature. Subsequently, the specimens were immersed in 20% sucrose (a product of Wako Pure Chemical Industries, Ltd.) in PBS while being refrigerated. When the brain specimens had sunk to the bottom of a specimen bottle, the specimens were immersed again in newly prepared 20% sucrose in PBS and similarly left to stand until they sank to the bottom of the specimen bottle. Containers which were one size larger than the brain specimens were made of aluminum foil and filled with a Tissue-Tek O.C.T. Compound (a product of Sakura Finetechnical Co., Ltd.), into which the brain specimens were placed. The brain specimens were then immersed in liquid nitrogen to freeze. Frozen brain specimen blocks were sliced into 10 μm-thick sections using a Cryostat microtome (a product of Leica Microsystems), which were collected onto prepared slides coated with aminosilane (a product of Matsunami Glass Ind., Ltd.). The prepared slides thus obtained were cryopreserved in a freezer at −80° C. until use. When using the cryopreserved prepared slides, they were rewarmed at room temperature for 30 minutes, followed by immersion in PBS at room temperature for 10 minutes.

In order to distinguish between a normal site and a demyelinating site, the specimens were immersed in a luxol fast blue staining liquid (0.1% luxol fast blue (a product of Acros Organics) in 95% ethanol (a product of Wako Pure Chemical Industries, Ltd.) containing 0.05% acetic acid (a product of Wako Pure Chemical Industries, Ltd.)) at 60° C. overnight and then washed with water, after which they were decolorized by a 0.05% lithium carbonate solution (a product of Wako Pure Chemical Industries, Ltd.) On that occasion, nuclear staining was performed with nuclear fast red (a product of Vector Laboratories, Inc.) After nuclear staining, the specimens were examined and imaged by a stereotactic light microscope (a product of Olympus Corporation).

Brain specimens adjacent to the demyelinating sites as confirmed above were selected and immersed in a 0.01 M citrate buffer solution (a product of Muto Pure Chemicals Co., Ltd.) immediately after boiling for 10 minutes and then immersed again in PBS in order to activate antigenicity against denaturation of antigens associated with postmortem change.

In order to confirm that Contactin molecules are highly expressed specifically in demyelinating sites and that an anti-Contactin antibody is specifically accumulated in the same sites, 10 μg/ml of mouse monoclonal anti-Contactin antibodies (a product of Becton, Dickinson and Company) in PBS containing 0.5% skim milk (a product of Difco Laboratories) was added to the brain specimens thus obtained, and the specimens were left to stand in a moist box for two days while being refrigerated at 4° C. Two days later, the specimens were washed by immersing in PBS for a total of three times, each continuing for three minutes. In order to visualize localization of an anti-Contactin antibody remaining after wash, the specimens were reacted with 10 μg/ml of fluorescein (FITC)-labeled goat polyclonal anti-mouse IgG antibodies (a product of The Jackson Laboratory) in PBS containing 0.5% skim milk at room temperature for two hours, after which the specimens were washed again by immersing in PBS for a total of three times, each continuing for three minutes. On that occasion, nuclear staining was performed with TO-PRO-3 (a product of Molecular Probes, Inc.). After wash, the specimens were sealed in Vectashield (a product of Vector Laboratories, Inc.), then examined and imaged by a confocal laser scanning microscope (a product of Nikon Corporation).

It is to be noted that when confirming localization of Contactin molecules on the surface of the demyelinating nerve axons, 10 μg/ml of mouse monoclonal anti-Contactin antibodies +10 μg/ml of rabbit polyclonal anti-Neurofilament antibodies (a product of AbD Serotec) in PBS containing 0.5% skim milk were administered instead of the above-described 10 μg/ml of mouse monoclonal anti-Contactin antibodies in PBS containing 0.5% skim milk, and for visualization of the above, a reaction was carried out using 10 μg/ml of FITC-labeled goat polyclonal anti-mouse IgG antibodies +10 μg/ml of indocarbocyanine (Cy3)-labeled goat polyclonal anti-rabbit IgG antibodies (a product of The Jackson Laboratory) in PBS containing 0.5% skim milk.

Results

Figure 2:
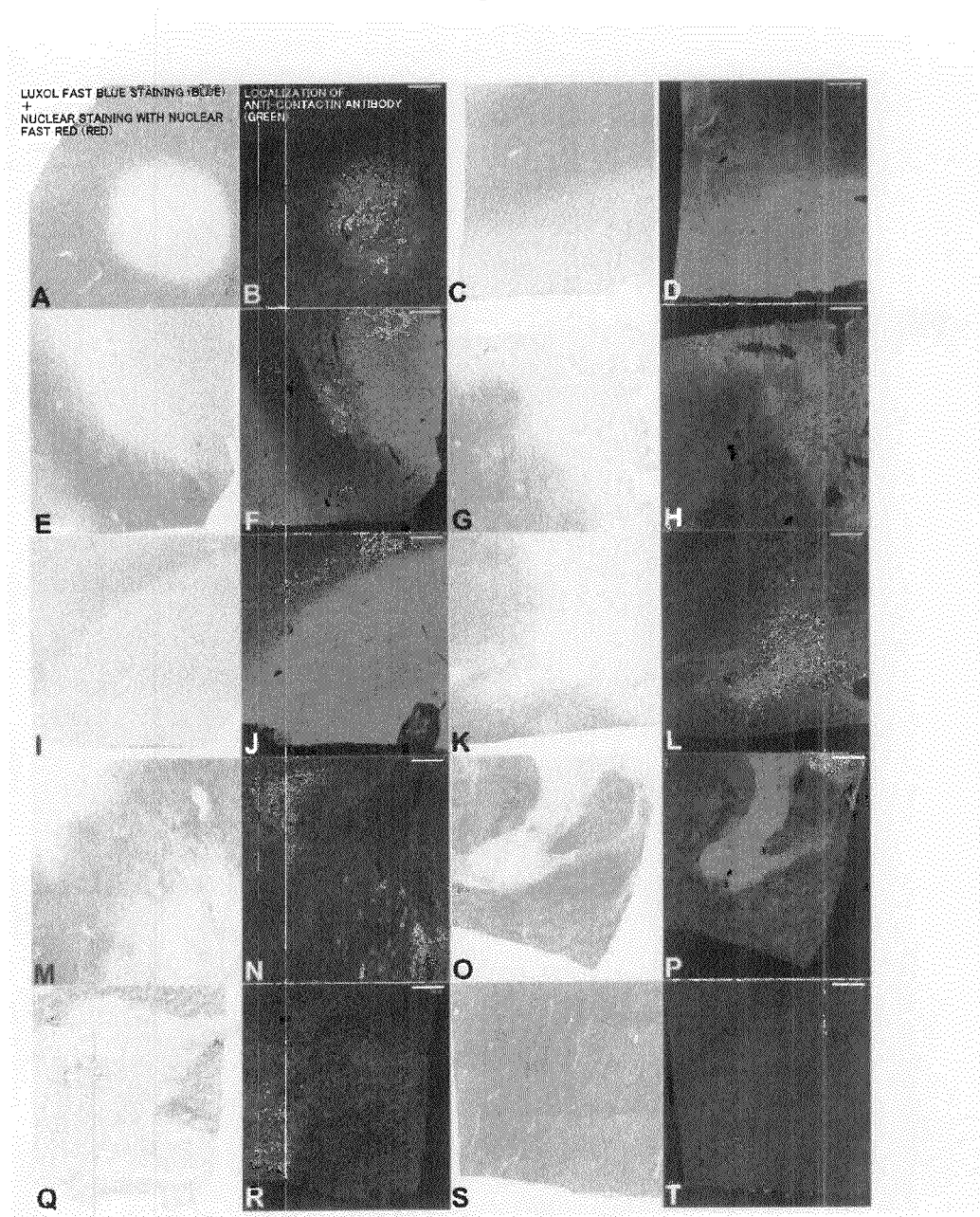
FIG. 2 shows nine cases of the brains of patients with multiple sclerosis (Panels A to R) and one case of the normal brain (Panels S and T). Panels A and B as well as Panels C and D show adjacent regions in an identical patient, and similarly Panels E to T also show two pictures in a set for a patient. As in FIG. 1, each Panel is intended to detect the demyelinating lesion by luxol fast blue staining (sites decolorized into white) and observe an accumulation of the anti-Contactin antibody in the demyelinating lesion similarly. Like a relationship between negative and positive images of a photograph, it is understood that the anti-Contactin antibody specifically accumulates in the demyelinating lesion in any of the brains of the patients with multiple sclerosis shown in Panels A to R. In contrast, neither the demyelinating lesion nor an accumulation of the anti-Contactin antibody is observed in the normal brain shown in Panels S and T. The above findings suggest that a pharmaceutical agent can be selectively accumulated in the demyelinating foci by a drug delivery targeting Contactin.
Figure 3:
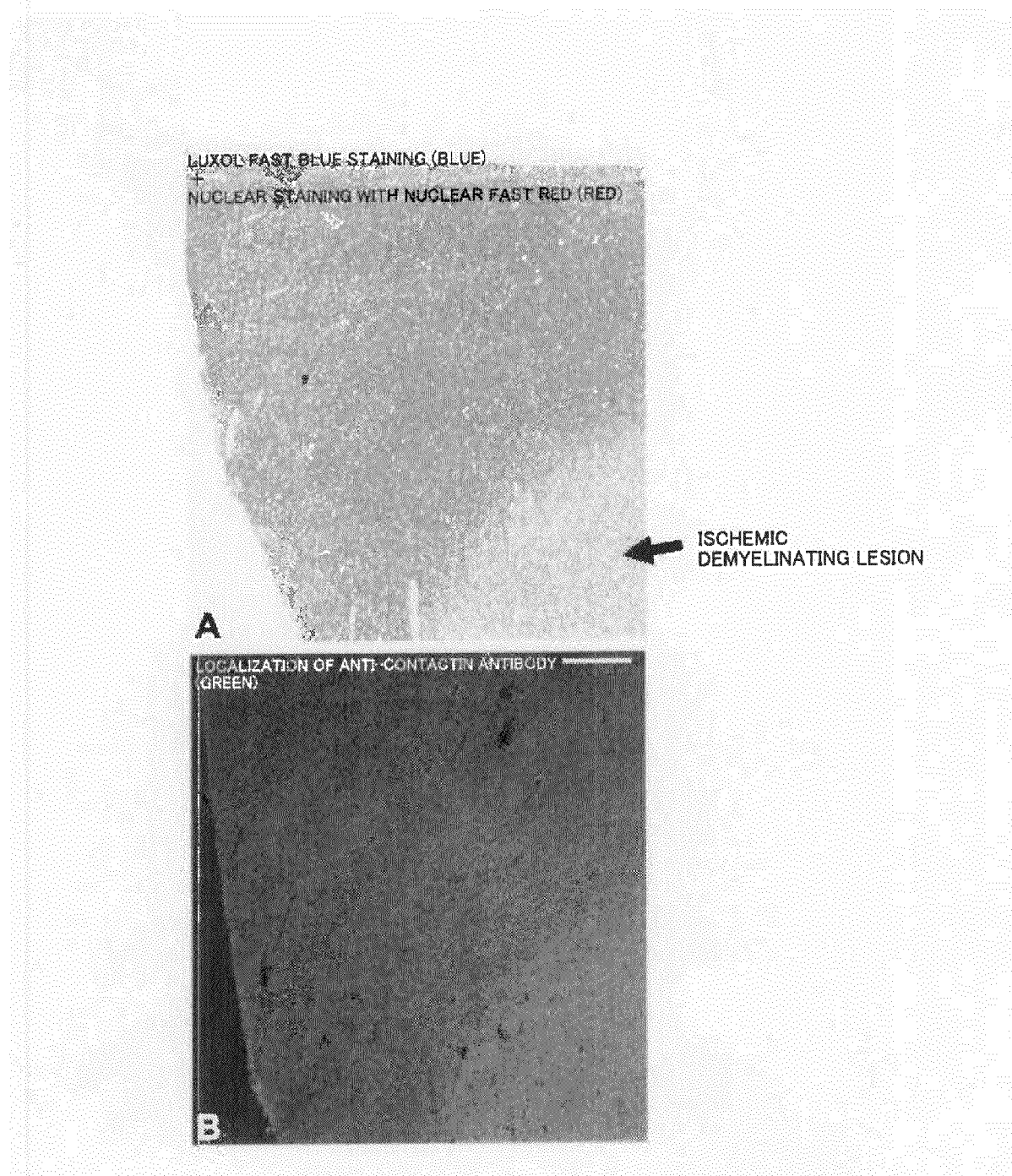
FIG. 3 shows a case of the brain of a patient with an ischemic encephalopathy. Like FIGS. 1 and 2.
Figure 4:
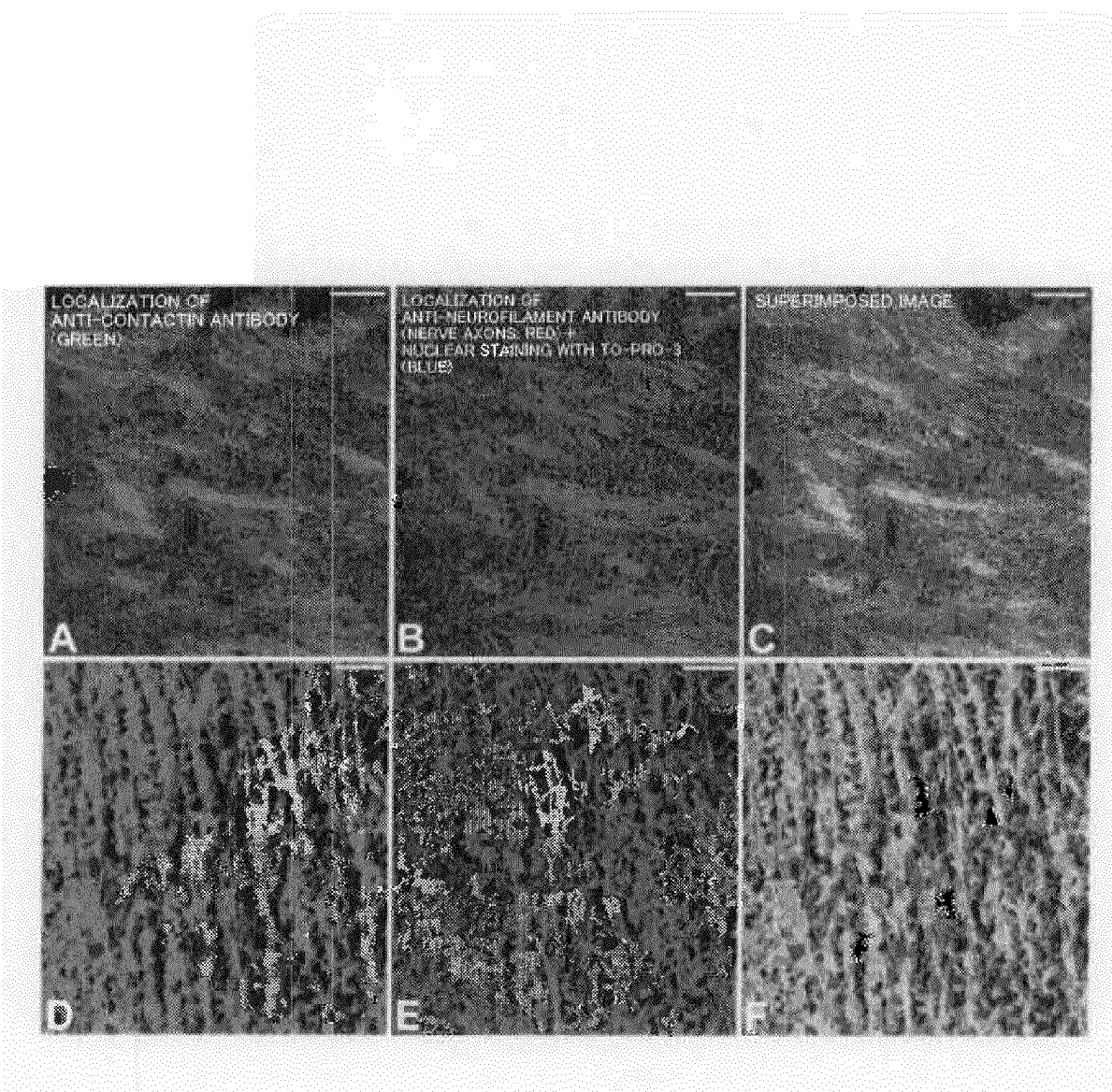
FIG. 4 shows two cases of the brains of patients with multiple sclerosis (Panels A to C, and Panels D to F). All Panels show the demyelinating lesions. In order to confirm that Contactin is expressed on the surface of the nerve axons in the demyelinating lesion, localization of the anti-Contactin antibody in the demyelinating lesion was similarly detected by a secondary antibody labeled with FITC as shown in FIGS. 1 to 3. Simultaneously, the same specimen was labeled by an anti-Neurofilament antibody recognizing Neurofilament, which was a marker of the nerve axons, and it was doubly detected by a secondary antibody labeled with Cy3. Panels A and D show localization of the anti-Contactin antibody and Panels B and E show localization of the anti-Neurofilament antibody, while Panels C and F show superimposed images of these pictures. Consequently, it was confirmed that localization of the anti-Contactin antibody was in correspondence to that of the anti-Neurofilament antibody (Panels A to C), and that the anti-Contactin antibody was localized on the surface of the nerve axons (Panels D to F). Accordingly, it was shown that a pharmaceutical agent could be selectively delivered to the periphery of the axons in the demyelinating lesions by a drug delivery targeting Contactin.

As shown in the case of staining of a brain of a patient with multiple sclerosis in FIG. 1-A, a myelin sheath is stained in blue by staining with luxol fast blue, and a nucleus is stained in red by nuclear staining with nuclear fast red. Sites decolorized into white correspond to demyelinating lesions in FIG. 1-A. FIG. 1-B represents a specimen adjacent to the specimen of FIG. 1-A, which was visualized by administration of an anti-Contactin antibody. The anti-Contactin antibody accumulates in an area corresponding to the demyelinating lesion in FIG. 1-A and is detected as green fluorescence. FIG. 2 shows similar results in nine cases of brains of patients with multiple sclerosis (A to P) and one case of a brain of a patient with no encephalopathy (S and T) (A/B, C/D, E/F, G/H, I/J, K/L, M/N, O/P, Q/R, and S/T are each adjacent specimens of the brain of an identical patient). As apparent in FIGS. 2-A to P, an anti-Contactin antibody localizes in the demyelinating lesion, whereas as apparent in FIGS. 2-S and T, the anti-Contactin antibody does not localize in the brain of the patient with no demyelination. Similar results were obtained in three other cases of brains of patients with no encephalopathy. As shown in FIGS. 3A and B, a secondary demyelinating lesion in ischemic encephalopathy (FIG. 3-A) is also characterized in that an anti-Contactin antibody localized in the demyelinating lesion (FIG. 3-B) as in the cases of multiple sclerosis. As shown in FIG. 4, an anti-Contactin antibody (FIGS. 4-A and D) is localized in nerve axons (FIGS. 4-B and E: Neurofilament is a normal constituent molecule of nerve axons and expressed in normal as well as demyelinating nerve axons) where an anti-Neurofilament antibody is localized (FIGS. 4-C and F).

Based on the above results, it was demonstrated that Contactin was highly expressed specifically in demyelinated axons regardless of the cause of demyelination, and a compound which molecularly targets Contactin (for example: an anti-Contactin antibody) specifically accumulated and localized in the demyelinated axons. Accordingly, it is suggested that a therapeutic agent and the like can be delivered specifically to a demyelinating lesion by using a compound which molecularly targets Contactin as a carrier.

Example 2

Biochemical Marker of Demyelinating Lesion

Method

A total of 120 samples including 30 cases of cerebrospinal fluids of patients with relapsing-remitting (relapsed phase) multiple sclerosis, 30 cases of cerebrospinal fluids of patients with relapsing-remitting (remission phase) multiple sclerosis, 30 cases of cerebrospinal fluids of patients with secondary-progressive multiple sclerosis, and 30 cases of cerebrospinal fluids of patients with other diseases (including patients with no encephalopathy, patients with ischemic encephalopathy, and the like) were provided by Human Brain and Spinal Fluid Resource Center in Los Angeles, Calif., U.S.A. The brain specimens were transported from the Center by air while kept frozen on dry ice, and preserved in a freezer at −80° C. immediately upon arrival at a laboratory in the Department of Anatomy, School of Medicine, Keio University.

Sandwich ELISA was used for quantitation of Contactin in the cerebrospinal fluids. As a capture antibody, goat polyclonal anti-Contactin antibody (a product of R&D systems, Inc.) in coating buffer solution (a product of KPL, Inc.) was prepared so as to have a concentration of 2 μg/ml and administered in a 96-well ELISA plate (a product of BD Falcon) at 100 μl/well, and a reaction was allowed to proceed at room temperature for two hours. The capture antibody was removed from all the wells using an ELISA plate washer (a product of Bio-Rad Laboratories), followed by administration of bovine serum albumin (BSA) blocking solution (a product of KPL, Inc.) at 200 μl/well. A reaction was allowed to proceed at room temperature for 10 minutes, after which the blocking solution was removed from all the wells using an ELISA plate washer again. Subsequently, cerebrospinal fluid specimens were administered to each well at 100 μl/well, or, as a control antigen for a standard curve, administered into recombinant human Contactin (a product of R&D systems, Inc.) in BSA diluent solution (a product of KPL, Inc.) at various concentrations, and reactions were allowed to proceed at room temperature for four hours. Upon completion of the reactions, all the wells were thoroughly washed by an ELISA plate washer using 1× wash solution (a product of KPL, Inc.). Following removal of the wash solution, mouse monoclonal anti-Contactin antibody (a product of Becton, Dickinson and Company) in BSA diluent solution was prepared so as to have a concentration of 1 μg/ml as a detector antibody and administered to each well at 100 μl/well, then a reaction was allowed to proceed at room temperature for two hours. Upon completion of the reaction, all the wells were thoroughly washed similarly to the above and peroxidase-labeled anti-mouse IgG antibody (a product of KPL, Inc.) was administered as a secondary antibody in accordance with the manufacturer's instructions. A reaction was then allowed to proceed at room temperature for one hour. Upon completion of the reaction, all the wells were thoroughly washed similarly to the above, and ABTS peroxidate substrate solution (a product of KPL, Inc.) was administered to each well at 100 μl/well and then a reaction was allowed to proceed at room temperature for 30 minutes. Upon completion of the reaction, peroxidase stop solution (a product of KPL, Inc.) was further administered at 100 μl/well, and finally the absorbance was measured at an absorption wavelength of 405 nm using an ELISA plate reader (a product of Bio-Rad Laboratories). The raw data thus obtained were converted to the concentration of Contactin by performing proportional calculation based on the standard curve on Microsoft Excel. However, cases in which any defect had been noticed in the original samples (cases of coloration, cases of bleeding, and the like) were excluded from assay.

Results

Figure 5:
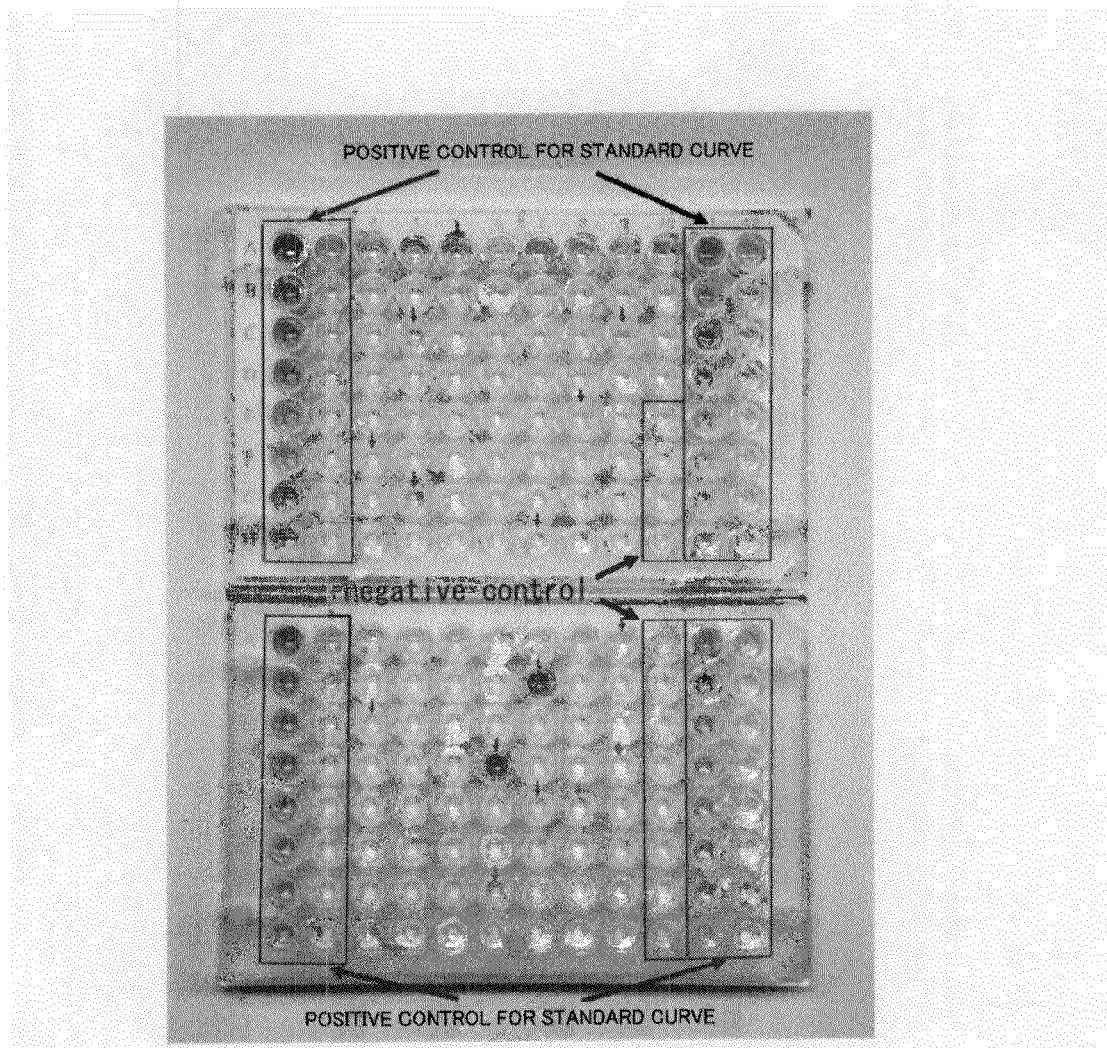
FIG. 5 shows Examples of quantitative assays of the concentration of Contactin in cerebrospinal fluid samples of patients with relapsing-remitting type (relapsed phase and remission phase) and secondary-progressive type of multiple sclerosis as well as patients with ischemic encephalopathies. Positive controls and negative controls used for quantitation were assayed in the positions shown in the Figure. The other positions contained cerebrospinal fluids of any one of the patients with diseases as described above. The wells indicated by arrows show a particularly strong positive response which could be confirmed visually as well (a dye was added so that a positive sample would be stained in green). Results of precise quantitation obtained by subjecting the device shown in the picture to an ELISA plate reader are shown in FIG. 6.
Figure 6:
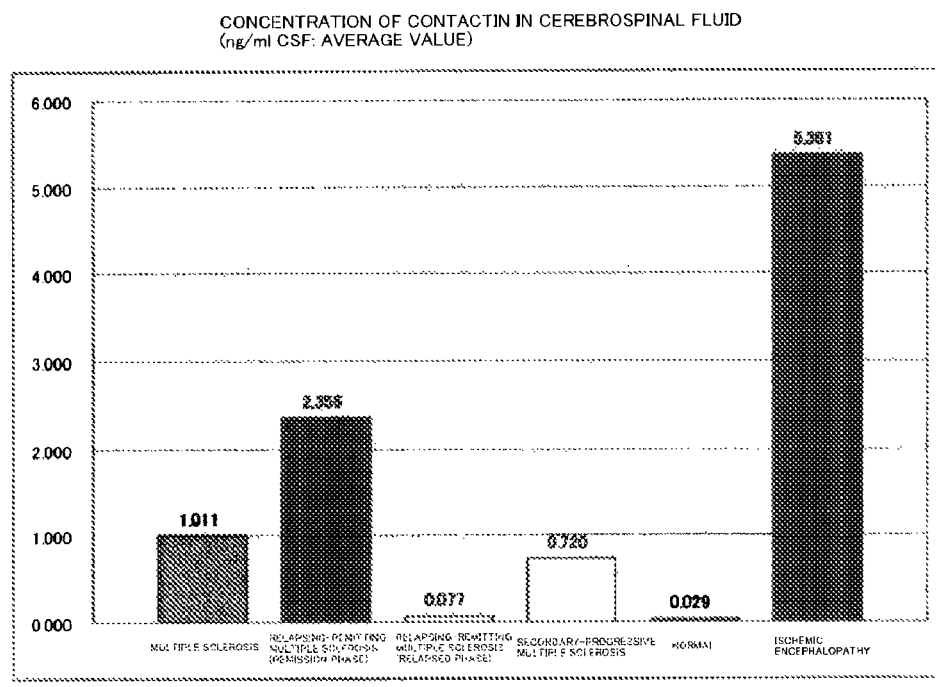
FIG. 6 is a graph showing an average value (a concentration in cerebrospinal fluid: ng/ml) in each disease group, as obtained by quantitating the results of FIG. 5 by an ELISA plate reader. The "multiple sclerosis" group shows an average value of data for all the groups of "relapsing-remitting multiple sclerosis (remission phase)", "relapsing-remitting multiple sclerosis (relapsed phase)", and "secondary-progressive multiple sclerosis", which are shown in three columns to the right of the "multiple sclerosis" group. As illustrated in this Figure, it is understood that Contactin is hardly detected in a normal sample, while it is detected in a sample involving demyelination such as multiple sclerosis and ischemic encephalopathies, from which it is understood that presence or absence of demyelination can be diagnosed by assaying the concentration of Contactin. Furthermore, it is shown that in multiple sclerosis, the concentration of Contactin is particularly high in the remission phase of relapsing-remitting multiple sclerosis, low in the remission phase, and moderate in the secondary-progressive multiple sclerosis. Hence, it was suggested that quantitation of Contactin was useful for diagnosis of a disease type.

After the reaction with ABTS, a plate was provided as shown in FIG. 5. Absorbance was measured and the concentration was calculated based on the standard curve, subsequently an average value was separately obtained from each group to give the results shown in FIG. 6. Namely, the average concentration of Contactin within cerebrospinal fluid in cerebrospinal fluids of patients with healthy brains ("normal") was 0.029 ng/ml, which was, in light of the error of the present examination, a hardly detected level. On the other hand, the average concentration of Contactin within cerebrospinal fluid in cerebrospinal fluids of patients with multiple sclerosis ("multiple sclerosis"), which was representative of demyelinating diseases, was 1.011 ng/ml, and that in cerebrospinal fluids of patients with ischemic encephalopathy ("ischemic encephalopathy") was 5.361 ng/ml. Concentrations of Contactin higher than normal were thus detected in the cerebrospinal fluids in these samples. Furthermore, when the cases of multiple sclerosis were classified according to the condition of disease, the concentrations of Contactin were found to be high in the remission phase of relapsing-remitting multiple sclerosis, low in the relapsed phase of relapsing-remitting multiple sclerosis, and moderate in secondary-progressive type. Hence, it was demonstrated that the concentration of Contactin in cerebrospinal fluid varies with the condition of disease.

Based on the results described as above, it was suggested that quantitative and qualitative evaluation, diagnosis and the like of demyelinating diseases would be possible by quantitating the concentration of Contactin in a body fluid (cerebrospinal fluid and the like) because Contactin was not released in cerebrospinal fluid in a normal brain, while it was released in cerebrospinal fluid when affected by demyelination, and further, because the concentration of Contactin varied with the condition of the disease.

All the literature, issued patents, and patent applications cited in the present specification are altogether incorporated in the present specification as references.

INDUSTRIAL APPLICABILITY

The present invention can be used for prophylaxis and treatment of a demyelinating disease.

Furthermore, the present invention can be used for evaluation and differentiation of a demyelinating disease.

The invention claimed is:

1. A method of evaluating and/or differentiating a demyelinating disease in a subject, comprising measuring Contactin levels in cerebrospinal fluid from said subject.

2. The method of claim 1, further comprising correlating the level of Contactin measured to evaluate and/or differentiate a demyelinating disease compared to a control sample.

3. The method of claim 1, wherein the measuring comprises contacting the cerebrospinal fluid with an antibody that specifically binds to Contactin.

4. The method of claim 2, wherein the measuring comprises contacting the cerebrospinal fluid with an antibody that specifically binds to Contactin.

5. The method of claim 1, wherein the demyelinating disease is one or more of congenital hypomyelinogenesis, demyelinating disease in the central nervous system, demyelinating disease in the peripheral nervous system, psychiatric disorder, post-radiation cephalopathy and post- chemotherapy cephalopathy.

6. The method of claim 2, wherein the demyelinating disease is one or more of congenital hypomyelinogenesis, demyelinating disease in the central nervous system, demyelinating disease in the peripheral nervous system, psychiatric disorder, post-radiation cephalopathy and post- chemotherapy cephalopathy.

* * * * *